United States Patent [19]

Satomura et al.

[11] Patent Number: 4,855,282

[45] Date of Patent: Aug. 8, 1989

[54] RECORDING MATERIAL AND METHOD FOR PRODUCING THE SAME

[75] Inventors: Masato Satomura; Ken Iwakura; Masanobu Takashima; Akira Igarashi, all of Shizuoka, Japan

[73] Assignee: Fuji Photo Film Co., Ltd., Kanagawa, Japan

[21] Appl. No.: 99,861

[22] Filed: Sep. 22, 1987

[30] Foreign Application Priority Data

Sep. 22, 1986 [JP] Japan .............................. 61-224611
Oct. 15, 1986 [JP] Japan .............................. 61-244987
Nov. 5, 1986 [JP] Japan .............................. 61-263034

[51] Int. Cl.$^4$ .................. B41M 5/16; B41M 5/18; B41M 5/22
[52] U.S. Cl. ................... 503/218; 427/150; 427/151; 428/913; 428/914; 503/220; 503/221; 503/223; 503/224
[58] Field of Search ............... 503/220, 218, 221, 223, 503/224; 427/150, 151; 428/913, 914

[56] References Cited

U.S. PATENT DOCUMENTS 4,007,317 2/1977 Sirothina et al. .................. 526/11.1
4,107,428 8/1978 Farber .............................. 503/220
4,751,213 6/1988 Satomura et al. .................. 503/218

FOREIGN PATENT DOCUMENTS 0127203 12/1984 European Pat. Off. ............ 503/220
0188377 7/1986 European Pat. Off. ............ 503/220

*Primary Examiner*—Bruce H. Hess
*Attorney, Agent, or Firm*—Sughrue, Mion, Zinn, Macpeak & Seas

[57] ABSTRACT

A recording material is disclosed, which comprises a support having thereon a recording layer containing an at least one electron-donating colorless dye and at least one electron-accepting compound, wherein said electron-donating colorless dye is a copolymer of at least one polymerizable colorless dye monomer and at least one comonomer. The recording material has improved color forming property, shelf life, and stability of colored images.

10 Claims, No Drawings

RECORDING MATERIAL AND METHOD FOR PRODUCING THE SAME

FIELD OF THE INVENTION

This invention relates to a recording material, and more particularly to a recording material improved in color forming property, shelf life, and stability of colored images.

BACKGROUND OF THE INVENTION

Recording materials using an electron-donating colorless dye and an electron-accepting compound have already found popular recognition as pressure-sensitive paper, heat-sensitive paper, light- and pressure-sensitive paper, electro thermo-recording paper, etc. For example, they are disclosed in detail in British Pat. No. 2,140,449, U.S. Pat. Nos. 4,480,052 and 4,436,920, Japanese Patent Publication No. 23922/85, and Japanese Patent Application (OPI) Nos. 179836/82, 123556/85, and 123557/85 (the term "OPI" as used herein refers to a "published unexamined Japanese patent application").

The recording materials must have properties of (1) producing a sufficiently high color density of the developed image at a sufficiently high speed, (2) forming no fog, (3) producing a developed imager which retains sufficient fastness after color development, (4) producing a developed image of an appropriate hue, and showing an aptitude for copying machines, (5) having a high signal to noise (S/N) ratio, (6) producing a developed color image having a sufficiently high chemical resistance, and so on. However, recording materials which satisfy all of these requirements to perfection have not been obtained yet.

In particular, studies on improvements in characteristics of such recording materials have been actively pursued in response to the speeding-up of the recording system and the diversification of requirements in recent years.

The present inventors have studied electron-donating colorless dyes and electron-accepting compounds with respect to such factors as oil solubility, degree of solubility in water, distribution coefficient, pKa, polarity of substituents, position of substituents, polymerizability, and alterations of crystallinity and solubility with a view to developing highly desirable recording materials and raw materials used therefor.

During the course of this study, they have studied the polymerization of a colorless dye, in order to develop of a polymerized colorless dye. Their invention relating to polymerization of a colorless dye having an amide group, which has high crystallinity, such as 2-acrylamide-6-diethylamino fluoran, etc. is the subject of co-pending U.S. patent application Ser. No. 06/872,785. As a result of further studies, it has now been found that a specific polymerized colorless dye, the dye of the present invention, manifests outstanding qualities.

Further, the method according to this invention exhibits a great advantage in the production of a dispersion for use in a recording material.

SUMMARY OF THE INVENTION

An object of this invention is to provide a recording material with excellent color forming property, shelf life, and stability of colored images.

Another object of this invention is to provide a simple method for the production of a dispersion for use in the recording material.

These and other objects and characteristics of the present invention will become apparent to one skilled in the art from the following description of preferred embodiments of the invention.

The objects of the invention described above have now been attained by a recording material comprising a support having thereon a recording layer comprising an at least one electron-donating colorless dye and at least one electron-accepting compound, wherein the electron-donating colorless dye is a copolymer of at least one polymerizable colorless dye monomer and at least one comonomer.

DETAILED DESCRIPTION OF THE INVENTION

The term "polymerizable colorless dye monomer (or more simply "polymerizable colorless dye")" as used in the present invention refers to an electron-donating colorless dye monomer containing at least one addition polymerizable group such as, for example, a vinyl group, an acrylic group, a methacrylic group, or an allyl group. The term "comonomer" as used herein refers to a monomer copolymerizable with the polymerizable colorless dye, containing at least one addition polymerizable group such as, for example, a vinyl group, an acrylic group, a methacrylic group, or an allyl group.

The polymerizable colorless dye preferably has an acrylic ester group, methacrylic ester group, allyl group or vinyl group, and more preferably has an acrylic ester group or methacrylic ester group.

Examples of the polymerizable colorless dye include triphenylmethane phthalide type compounds, fluoran type compounds, phenothiazine type compounds, indolyl phthalide type compounds, leucoauramine type compounds, rhodamine lactam type compounds, triphenyl methane type compounds, triazene type compounds, and spiropyran type compounds substituted with the above-described addition polymerizable groups.

The polymerizable colorless dye of this invention can be synthesized by reacting (a) a compound having an active group such as vinyl group-containing acid halide, ester, halide or isocyanate with (b) a colorless dye nucleus having at least one active hydrogen atom, in a group such as a hydroxy group or amino group.

Examples of compound (a) having an active group include acrylic acid chloride, methacrylic acid chloride, glycidyl acrylate, β-bromoethyl methacrylate, glycidyl methacrylate, p-methacryloyloxybenzoyl chloride, methacryloyloxyacetyl chloride, p-methacryloyloxyphenylthioacetyl chloride, β-methacryloyloxyethyltosylate, β-acryloyloxyethyl-p-tosylate, β-methacryloyloxypropyl-p-tosylate, diethylene glycol monomethacrylate monotosylate, vinylbenzoic acid chloride, vinylbenzene sulfonyl chloride, vinylbenzyl chloride, vinyl methyl benzoate, vinyl phenoxyacetyl chloride, and γ-acryloyloxypropyl isocyanate.

Alternatively, the polymerizable colorless dye can be synthesized by a method which uses a vinyl group-containing intermediate for a coloring agent as a starting material.

The active group in compound (a), such as a vinyl or vinylidene group, may be directly bonded to the aromatic ring of the colorless dye nucleus or can be substituted for an active hydrogen thereof. It may otherwise be bonded thereto through a linking group, such as an alkylene group having 1 to 12 carbon atoms, which may include at least one oxygen or sulfur atom, an arylene group, or a group combining two or more of such groups.

Examples of the active group with the linking group include an acryloyloxy group, a methacryloyloxy group, a vinylbenzoyloxy group, a vinylphenoxyacetoxy group, a methacryloyloxyethoxy group, an acryloyloxyethoxy group, a vinylbenzenesulfonyloxy group, an allyloxy group, an acryloyloxypropoxy group, a methacryloyloxypropoxy group, a 5-methacryloyloxy-3-oxapentyl group, a 5-acryloyloxy-3-oxapentyl group, a p-methacryloyloxybenzoyloxy group, a β-acrylamide ethyl group, a β-N-ethyl-N-acrylamide ethyloxy group, a vinyloxyethoxy group, a vinylanilinocarbonyloxy group, a β-methacryloyloxybutoxy group, a γ-acryloyloxypropoxy group, a vinylbenzyloxy group, a δ-metharyloylaminobutoxy group, a β-acryloylaminoethoxy group, a β-p-vinylbenzoyloxyethoxy group, a γ-vinylphenoxy-β-hydroxypropoxy group, a β,γ-dimethacryloyloxypropoxy group, a glycidyloxy group, and a β-vinylpyhenoxyethoxy group.

The number of vinyl groups is preferably one or two.

Among these active groups capable of bonding to the aromatic ring of the colorless dye nucleus or of being substituted at the position having an active hydrogen thereof, acrylic esters and methacrylic esters are preferred in that they have high solubility and low melting points and are easily copolymerized.

In the polymerizable colorless dyes used in the present invention, those colorless dyes which have a compound having an active group such as an acrylic ester, or methacrylic ester bonded through a linking group such as alkylene which may include at least one oxygen or sulfur atom, alkenylene, or arylene to the basic dye moiety thereof (i.e., the structures which determine the hue of color generated on contact with an electron accepting compound) are particularly preferred.

Specifically, preferred polymerizable colorless dye monomer according to the present invention is represented by formula (I):

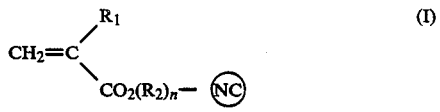
(I)

wherein $R_1$ represents a hydrogen atom, a methyl group or an ethyl group, $R_2$ represents an alkylene group which may include at least one oxygen or sulfur atom, an alkenylene group, or an arylene group, each having 2 to 10 carbon atoms, n is 0 or 1, and ⓝⓒ represents a basic dye moiety of a known non-polymeric colorless dye such as, for example, triphenyl methane phthalide type compounds, fluoran type compounds, phenothiazine type compounds, indolyl phthalide type compounds, leucoauramine type compounds, rhodamine lactam type compounds, triphenyl methane type compounds, and triazene type compounds.

These known non-polymeric colorless dyes are disclosed in U.S. Pat. Nos. 3,491,111, 3,491,112, 3,491,116, 3,509,174, 3,624,107, 3,627,787, 3,641,011, 3,462,828, 3,681,390, 3,920,510, 3,959,571, 3,971,808, 3,775,424, 3,853,869, and 4,246,318.

Preferred non-polymeric colorless dyes include phthalide type colorless dyes represented by formula (II):

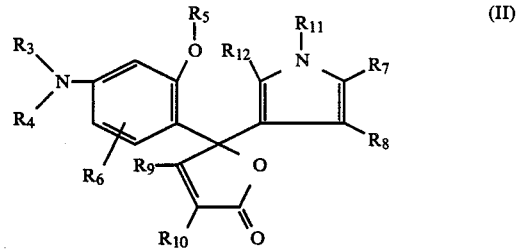

wherein $R_3$ through $R_{12}$, which may be the same or different, each represents a hydrogen atom, a halogen atom, an alkyl group, an alkoxy group, a substituted amino group, or an aryl group, provided that $R_7$ and $R_8$ may be linked to form a ring, and $R_9$ and $R_{10}$ may be linked to form a ring.

Specific examples of the ring formed by $R_7$ and $R_8$, or $R_9$ and $R_{10}$ include single or condensed aromatic rings such as a benzene ring, a pyridine ring, a pyrazine ring, a pyrimidine ring, a quinoline ring, a naphthalene ring, a benzofuran ring, and a benzothiophene ring.

The substituted amino group is an alkylamino or arylamino group having 1 to 12 carbon atoms, which may be substituted with, for example, a phenyl group, a pyridyl group, a furfuryl group, a hydroxy group, an acyl group, an alkoxy group, a cyano group, or a nitro group, and may form a ring such as a morpholino, piperidino or hexamethylene imino ring.

Specific examples of the substituted amino group include an alkylamino group, a dialkylamino group, an N-arylalkylamino group, an N-diethylamino group, an N-phenylethylamino group, a dibutylamino group, a dibenzylamino group, an N-isoamylethylamino group, and an N-furfurylmethylamino group.

It will be readily understood from the foregoing description that compounds represented by formula (I) are easily obtained by substituting

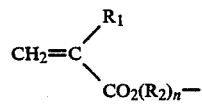

for the active hydrogen-containing group of the aforementioned non-polymeric colorless dyes.

Thus, the polymerizable colorless dyes according to the invention can be obtained by replacing the group which may be an active hydrogen atom of the non-polymeric colorless dyes mentioned above with a group having an addition polymerizable group, preferably a (meth)acryloyloxyalkyl or (meth)acryloyloxyaryl group.

According to the present invention, the group which may be an active hydrogen atom, preferably $R_3$, $R_4$, $R_5$ or $R_{11}$ of the compound represented by formula (II) is substituted with

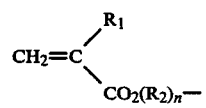

(wherein $R_1$, $R_2$ and n are defined as above) as shown in the following formulae (II-1) to (II-4). In these formulae, the polymerizable groups are represented by a methacryloyloxyethyl group, although the present invention is not to be construed as being limited thereto.

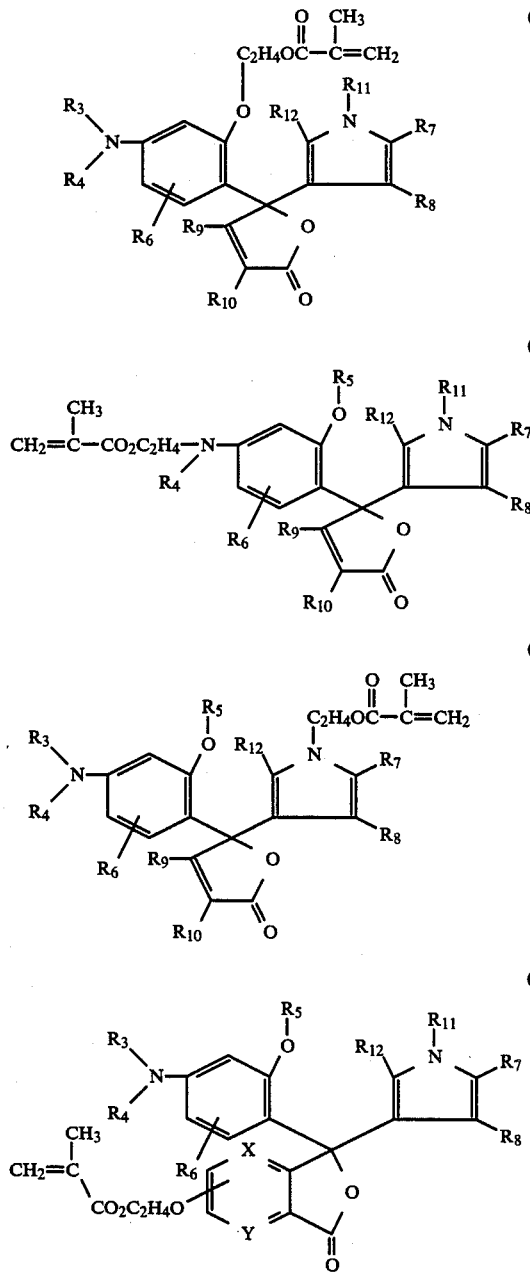

In Formula (Ii-4), X and Y each represents —N═ or —CH═.

These formulae clearly show that the group which may be an active hydrogen atom of the non-polymeric electron-donating colorless dye nucleus can be substituted with an addition polymerizable group to form the polymerizable colorless dye according to the invention.

Typical examples of the polymerizable colorless dye according to the invention include the following compounds.

(1) 3-(4-Diethylamino-2-methacryloyloxyphenyl)-3-(1-ethyl-2-methylindol-3-yl)phthalide (2) 3-[4-Diethylamino-2-p-vinylbenzyloxyphenyl]-3-(1-methyl-2-methylindol-3-yl)phthalide.

(3) 3-[4-Diethylamino-2-(acryloyloxyethoxy)phenyl]-3-(1-octylindol-3-yl)phthalide (4) 3-[4-Diethylamino-2-(methacryloyloxyethoxy)phenyl]-3-(1-benzylindol-3-yl)phthalide (5) 3-[4-Dimethylamino-2-($\beta$-acryloyloxyethoxy)phenyl]-3-(1-methyl-2-methylindol-3-yl)-azaphthalide 3-[4-Dibutylamino-2-$\beta$-acryloyloxyethylamidoethoxyphenyl)-3-(1-ethyl-2-methylindol-3-yl) diazaphthalide (7) 3-(4-Diethylamino-2-vinylbenzyloxyethoxyphenyl)-3-(1,2-dimethylindol-3-yl)phthalide (8) 3-(4-Diethylamino-2-$\beta$,$\gamma$-dimethacryloyloxypropoxyphenyl)-3-(1-ethyl-2-phenylindol-3-yl) phthalide (9) 3-[4-Diethylamino-2-($\beta$-acryloyloxypropyloxy)phenyl]-3-(1-ethyl-2-methylindol-3-yl)4-azaphthalide

(10) 3-[4-Diethylamino-2-vinylbenzenesulfonylamide)phenyl]-3-(1-ethyl-2-methylindol-3-yl)-4-azaphthalide

(11) 3-[4-Diethylamino-2-($\beta$-vinylphenoxy)phenyl]-3-(1-ethyl-2-iso-pentylindol-3-yl)-4-aza-phthalide

(12) 2-$\beta$-Methacryloyloxyethylamino-6-diethylaminofluoran

(13) 2-$\beta$-Methacryloyloxyethylamino-3-methyl-6-diethylaminofluoran

(14) 2-$\beta$-Methacryloyloxyethylamino-3-chloro-6-diethylaminofluoran

(15) 2-N-Ethyl-$\beta$-methacryloyloxyethylamino-6-dimethylaminofluoran.

(16) 2-N-Methyl-$\beta$-methacryloyloxyethylamino-3-methyl-6-diethylaminofluoran

(17) 2-p-N-Methyl-$\beta$-methacryloyloxyethylaminoanilino-3-methyl-6-dimethylaminofluoran

(18) 2-$\beta$-Methacryloyloxyethoxyanilino-3-methyl-6-diethylaminofluoran

(19) 2-Anilino-3-methyl-6-N-ethyl-$\beta$-methacryloyloxyethylaminofluoran

(20) 2-Anilino-3-methyl-6-diethylamino-4'-methacryloyloxyethoxyfluoran.

(21) 2-p-Vinylbenzylamino-3-methyl-6-diethylaminofluoran.

(22) 2,2'-Dibenzylamino-6-N-ethyl-$\beta$-methacryloyloxyethylaminofluoran.

(23) 3-Ethoxy-6-$\beta$-methacryloyloxyethoxyfluoran

(24) 3-$\beta$-Phenylethoxy-6-$\beta$-methacryloyloxypropoxyfluoran

(25) 4-Diethylaminophenyl-4'-N-ethyl-N-$\beta$-methacryloyloxyethylaminophenyl phthalide

(26) 2-p-Vinylbenzoyloxy-4-diethylaminophenyl-2'-p-vinylbenzoyloxy-4'-methyl-5'-anilinophenyl phthalide

(27) 2-$\beta$-Methacryloyloxyethylureido-6-diethylaminofluoran

(28) 2-p-Methacryloyloxyanilino-3-methyl-6-diethylaminofluoran

(29) 2-Anilino-4-$\gamma$-p-vinylbenzoylaminobutyl-6-diethylaminofluoran

(30) 2-$\beta$-Hydroxy-$\gamma$-p-methacryloyloxyphenylthioacetylamino-6-diethylaminofluoran

(31) 3-(4-Diethylamino-2-methacryloyloxyphenyl)-3-(1-methacryloyloxyethyl-2-methylindol-3-yl)phthalide

(32) 3-[4-Diethylamino-2-p-vinylbenzyloxyphenyl]-3-(1-vinylbenzyl-2-methylindol-3-yl)phthalide

(33) 3-(4-Diethylamino-2-β,γ-dimethacryloyloxypropoxyphenyl)-3-(1-ethyl-2-phenylindol-3-yl)phthalide

(34) 3-[4-Diethylamino-2-(β-acryloyloxypropyloxy)phenyl]-3-(1-ethyl-2-methylindol-3-yl)4-azaphthalide

(35) 3-[4-Diethylamino-2-(β-vinylphenoxyethoxy)phenyl]-3-(1-ethyl-2-iso-pentylindol-3-yl)-4-azaphthalide

(36) 3,3-bis(p-Dimethylaminophenyl)-6-N-ethyl-N-β-methacryloyloxyethylaminophthalide

(37) 3,3-bis(p-Diethylaminophenyl)-6-N-ethyl-N-vinylbenzylaminophenyl phthalide

(38) p-Vinylbenzoyl leucomethylene blue

(39) Methacryloyloxyethyloxyacetyl leucomethylene blue

(40) 3-(4-Diethylamino-2-β-methacryloyloxyethoxyphenyl)-3-(1-ethyl-2-methylindol-3-yl)phthalide

(41) 3-(4-Diethylamino-2-β-methacryloyloxyethoxyphenyl)-3-(1-octyl-2-methylindol-3-yl)phthalide

(42) 3-(4-Diethylamino-2--vinylbenzyloxyphenyl)-3-(1-ethyl-2-methylindol-3-yl)phthalide In the present invention, at least one vinyl group-containing polymerizable colorless dye monomer described above is copolymerized with a comonomer having an addition polymerizable group such as a vinyl or vinylidene group. Examples of the comonomer include amides, ethers, esters, and aromatics which have addition polymerizable groups. The compounds which are obtained by the reaction of polyamines, polyols, and amino alcohols with allyl halides, (meth)acrylic acid chlorides, or (meth)acrylic acid esters are preferred.

The particle diameter, solubility, viscosity, dispersion stability, color forming property, etc. of the produced copolymer can be freely controlled by selecting the amounts and kinds of the comonomers used. The amount of copolymer present can be varied widely, but the copolymer must contain at least about 5 mol % of the colorless dye monomer which is capable of forming a colored dye on contact with an acidic compound (an electron-accepting compound).

The ratio of the comonomer used to react with the polymerizable colorless dye monomer is preferably 80 mol % or less, and more preferably 50 mol % or less.

The ratio of the polymerizable colorless dye monomer is preferably 10 to 80 mo%.

Specific examples of the comonomer copolymerized with the polymerizable colorless dye include acrylamide, cellosolve acrylate, styrene, methyl methacrylate, acrylonitrile, vinyl carbazole, octyl acrylate, sodium acrylamide-propanesulfonate, butyl methacrylate, ethyl acrylate, divinyl benzene, vinyl dioxolane, epichlorohydrin, allyl methacrylate, cinnamoyloxyethyl methacrylate, vinylbenzophenone, ethylene glycol diacrylate, diethylene glycol diacrylate, diethylene glycol monoacrylate, chloromethyl styrene, methacrylamide, cellosolve acrylate, chlorostyrene, oleyl methacrylate, methacrylonitrile, 6-cyano-vinyl carbazole, triethylene glycol (meth)acrylate, triemthylol propane di(meth)acrylate, pentaerythritol tri(meth)acrylate, β-phenylureido ethylacrylate, acrylic acid 2-ethylhexyl acrylamide calcium propanesulfonate, butyl methacrylate, ethyl acrylate, divinyl toluene, ethyl cellosolve acrylate, methallyl methacrylate, α-cyanocinnamoyloxybutyl methacrylate, β-phenoxyethyl methacrylate, and triethylene glycol diacrylate. These comonomers can be used alone or in combination. Among these comonomers, at least one acrylic ester or methacrylic ester is preferably used.

As to the polymerization method, radical polymerization which includes solution polymerization, emulsion polymerization, suspension polymerization, etc. is preferably used.

To be more specific, the radical polymerization which is preferred in the present invention can be initiated by the use of a radical polymerization initiator. A perslfate reducing agent, an oily or aqueous azo compound, a peroxide, or a metallic catalyst may be used as the initiator. The polymerization reaction is desirably carried out under an atmosphere of an inert gas. Where the polymerization requires application of heat, the heating temperature is preferably below about 120° C., more preferably below about 90° C.

The polymerization can be carried out, when necessary, in a solvent. Examples of useful solvents include polar solvents such as water, esters, ethers, halides, ketones, amides, and alcohols and non-polar solvents such as hydrocarbons and aromatics. These solvents can be used alone or in combination.

Various non-polymeric colorless dyes can be added to the polymerization system, during the course of the reaction, for the purpose of improving the copolymer produced in hue and efficiency of coloration.

Among other copolymers according to this invention, those produced by polymerization, especially emulsion polymerization, in an aqueous medium in the presence of a radical polymerization catalyst are particularly preferred.

As to the method of emulsification, the method of degas, the control of reaction temperature, the method of handling a metallic catalyst, the method of post-treatment of the product fresh from polymerization, and the method of refining the produced polymer which are used during the course of the polymerization reaction described above, conventional copolymerization reaction techniques can be advantageously followed with necessary modifications. The general method of polymerization, for example, is described in detail in Sorensen, *Preparative Methods of Polymer Chemistry*, Tokyo Kagakudojin (1966), and Braun et al, *Praktikum der Makromolecularen Orqanischen Chemie*, Asakura Shoten (1968).

The colorless dye polymer obtained can be used in combination with any of conventional colorless dyes such as, for example, non-polymeric colorless dyes like CVL (Crystal Violet lactone) and BLMB (benzoyl leuco methylene blue) disclosed in the aforementioned patents as showing various hues, for the purpose of enhancing depth of color hue and enriching color variation. The non-polymeric colorless dyes are preferably used in an amount of 160 wt % or less, and more preferably 40 wt % or less, of the colorless dye polymer of the present invention.

When the colorless dye and an electron-accepting compound are used for a recording material, they are prepared in the form of fine dispersions or fine droplets.

Their use in this particular form is important for the purpose of increasing as much as possible the surface area of the materials, a factor contributing to the color formation reaction, enhancing the frequency and chance of contact between the colorless dye and the electron-accepting compound, and imparting high sensitivity to the recording material. Generally, the electron-donating colorless dye and the electron-accepting compound are ground to a particle diameter of not more than about 10 μm, preferably not more than about 3 μm, and dispersed in a dispersing medium, to be used advantageously in the preparation of the recording material. As to the dispersing medium, generally a water-soluble high-molecular dispersing medium prepared in the form of an aqueous solution containing the medium in a concentration of about 0.25 to 10% is used.

Although dispersion of the medium in water can be effected by the use of a ball mill, a sand mill, a horizontal sand mill such as Dyno Mill ®, or an attritor, any method of dispersion which requires use of such media as balls, sand grains, or flint stones has a serious drawback.

For a given material to be dispersed in a finely divided state, the individual particles of the dispersing medium to be distributed at as small an interval as possible, and this inevitably results in increasing the load, requires use of a huge apparatus, complicates the handling of materials, and entails gradual loss of the medium with the lapse of treating time.

The dispersion of a colorless dye finely divided by the use of a sand mill, for example, is obtained as follows. In a mill, fine sand grains are rotated at a high speed in such a manner that the sand grains in motion collide against one another and exert a violent impact upon the colorless dye, resulting that the colorless dye is finely divided and dispersed uniformly to produce a dispersion of colorless dye.

In the produced dispersion, therefore, finely divided particles of sand and colorless dye coexist are present with worn sand grains and fragmented sand grains.

For the separation of the desired product from this dispersion, therefore, a specialized separation technique is required. Thus, dispersion by the use of a sand mill is not practicable from a commercial point of view. The presence of hard sand grains in any event is undesirable in a coating liquid.

The conversion of the raw material for the recording material into fine particles is important to provide high sensitivity to the recording material produced.

The method of this invention easily produces a dispersion containing the raw material in an extremely finely divided state, without any such mechanical step of comminution as described above, which is one of the characteristic features of method of the present invention.

It is surprising that by employing emulsion polymerization, colorless dye polymer particles measuring not more than about 1 μm in average diameter are obtained without the use of any of the conventional dispersing machines such as a ball mill, a sand mill and the like.

For production of the colorless dye polymer of the present invention, it is important that a polymerizable colorless dye monomer containing an active group such as an acrylic ester or methacrylic ester and a comonomer should be reacted in the presence of a radical polymerization catalyst at a pH value of at least about 6 in the presence of a surfactant.

If the pH value is below about 5.5, the colorless dye polymer produced is seriously colored. If the surfactant present in the polymerization system does not have a concentration not less than about $10^{-5}$ mol %, preferably not less than about $10^{-3}$ mol %, (based on the amount of the polymerizable colorless dye), the colorless dye polymer produced is liable to undergo conglomeration. During the course of the copolymerization reaction, the solids concentration in the reaction system is preferably not less than about 5 wt %. In emulsion polymerization it is preferred to use a monomer and/or a solvent capable of dissolving the colorless ldye in not less than about 5 wt %.

A water-soluble solvent is used particularly advantageously in the present invention. Examples of the water-soluble solvent include alcohols, ethers, ketones, and nitrile compounds. The polymerizable colorless dye of the present invention is easily emulsified and dispersed, handled easily, and not easily conglomerated as compared with a polymerizable colorless dye containing an acrylic acid amide group, and is highly crystalline and sparingly soluble.

As already described, during the course of the copolymerization reaction or during the preparation of the dispersion for the production of the recording material, a non-polymeric colorless dye varying hue may be added to the reaction system.

Conventional non-polymeric colorless dyes include phthalide type compounds disclosed in U.S. Reissue Pat. No. 23,024, U.S. Pat. Nos. 3,491,111, 3,491,112, 3,491,116, and 3,509,174; fluoran type compounds disclosed in U.S. Pat. Nos. 3,624,107, 3,627,787, 3,641,011, 3,462,828, 3,681,390, 3,920,510, and 3,959,571; spirodipyrane type compounds disclosed in U.S. Pat. No. 3,971,808; and pyridine or pyradine type compounds disclosed in U.S. Pat. Nos. 3,775,424, 3,853,869, and 4,246,318.

Specific examples of the non-polymeric colorless dye include triarylmethane compounds such as 3,3-bis(p-dimethylaminophenyl)-6-dimethylaminophthalide (i.e., crystal violet lactone), 3,3-bis-(p-dimethylaminophenyl)phthalide, 3-(p-dimethylaminophenyl)-3-(1,3-dimethylindol-3-yl)phthalide, and 3-(p-dimethylaminophenyl)-3-(2-methylindol-3-yl)phthalide; diphenylmethane type compounds such as 4,4'-bis-dimethylaminobenzhydrin benzyl ether; leucoauramine type compounds such as N-halophenylleucoauramine, and N-2,4,5-trichlorophenyl leucoauramine; rhodamine lactam type compounds such as rhodamine-B-anilinolactam, rhodamine-(p-nitroanilino)lactam, and rhodamine B-(p-chloroanilino)lactam; fluoran type compounds such as 2-dibenzylamino-6-diethylaminofluoran, 2-anilino-6-diethyl-aminofluoran, 2-anilino-3-methyl-6-diethylaminofluoran, 2-anilino-3-methyl-6-cyclohexylmethylaminofluoran, 2O-chloroanilino-6-diethylaminofluoran, 2-m-chloroanilino-6-diethylaminofluoran, 2-(3,4-dichloroanilino-6-diethylaminofluoran, 2-octylamino-6-diethylaminofluoran, 2-dihexylamino-6-diethylaminofluoran, 2-m-trifluoro-methylanilino-6-diethylaminofluoran, 2-butylamino-3-chloro-6-diethylaminofluoran, 2-ethoxyethylamino-3-chloro-6-diethylaminofluoran, 2-p-chloroanilino-3-methyl-6-dibutylaminofluoran, 2-anilino-3-methyl-6-dioctylaminofluoran, 2-anilino-3-chloro-6-diethylaminofluoran, 2-diphenylamino-6-diethylaminofluoran, 2-anilino-3-methyl-6-diphenylaminofluoran,2-phenyl-6-diethylaminofluoran, 2-anilino-3-methyl-6-N-ethyl-N-isoamylaminofluoran, 2-anilino-3-methyl-5-chloro-6-diethylaminofluoran, 2-anilino-3-methyl-6-diethylamino-7-methylfluoran, 2-anilino-3-methoxy-6-dibutylaminofluoran, 2-o-chloroanilino-6-dibutylaminofluoran, 2-p-chloroanilino-3-ethoxy-6-N-ethyl-N-isoamylaminofluoran, 2-o-chloroanilino-6-p-butylanilinofluoran, 2-anilino-3-pentadecyl-6-diethylaminofluoran, 2-anilino-3-ethyl-6-dibutylaminofluoran, 2-anilino-3-methyl-4',5'-dichlorofluoran, 2-o-toluidino-3-methyl-6-diisopropylamino-4',5'-dimethylaminofluoran, 2-anilino-3-ethyl-6-N-ethyl-N-isoamylaminofluoran, 2-anilino-3-methyl-6-N-ethyl-N-

γ-methoxypropylaminofluoran, and 2-anilino-3-chloro-6-N-ethyl-N-isoamylaminofluoran; thiazine type compounds such as benzoyl leucomethylene blue and p-nitrobenzoyl leucomethylene blue; and spiro type compounds such as 3-methyl-spiro-dinaphthopyrane, 3-ethyl-spiro-dinaphthopyrane, 3,3'-dichloro-spiro-dinaphthopyrane, 3-benzyl-spiro-dinaphthopyrane, 3-methylnaphtho-(3-methoxy-benzo)-spiro-pyrane, and 3-propylspiro-dibenzopyrane. It is preferred to use at least two of these compounds in combination.

The electron-accepting compound which forms a color on contact with the electron-donating colorless dye polymer can be any of the conventional developer compounds known to be capable of color formation, as described in U.S. Pat. Nos. 3,491,111, 3,491,112, 3,491,116, 3,509,174, 3,624,107, 3,627,787, 3,641,011, 3,462,828, 3,681,390, 3,920,510, 3,959,571, 3,971,808, 3,775,424, 3,853,869, 4,246,318, 4,480,052, and 4,436,920, British Pat. Nos. 2,140,449, 1,018,793, 2,166,882, 2,165,953, 2,162,650, 2,156,535, and 2,154,014, Japanese Patent Publication No. 23922/85, and Japanese Patent Application (OPI) Nos. 179836/82, 123556/85, and 123557/85. Examples of the electron-accepting compound include phenol derivatives, salicylic acid derivatives, metal salts of aromatic carboxylic acids, and acid clay.

Specific examples of the electron-accepting compound include organic developers such as 4-tertiary butyl phenol 4-phenylphenol, 2, 2-bis(4-hyeroxyphenyl)propane (i.e., bisphenol A), 4,4'-isopropylidene-bis(2-methylphenol), 1,1-bis(3-chloro-4-hydroxyphenyl)cyclohexane, 1,1-bis(3-chloro-4-hydroxyphenyl)-2-ethyl butane, 4,4'-secondary isooctylidene diphenol, 4-tert-octyl phenol, 4,4'-sec-butylidene diphenol, 4-chlorophenylphenol, 4,4'-isopentylidene diphenol, 4,4'-methylcyclohexylidene diphenol, 4,4'-dihydroxydiphenyl sulfide, 1,4-bis-4'-hydroxycumyl benzene, 1,3-bis-4'-hydroxycumyl benzene, 4,4'-thiobis(6-tert-butyl-3-methyl phenol), 4,4'-dihydroxydiphenyl sulfone, hydroquinone monobenzyl ether, 4-hydroxybenzophenone, 2,4-dihydroxybenzophenone, polyvinyl benzyloxycarbonyl phenol, 2,2',4,4'-tetrahydroxybenzophenone, dimethyl 4-hydroxyphthalate, methyl 4-hydroxybenzoate, 2,4,4'-trihydroxydiphenyl sulfone, 1,5-bis-p-hydroxyphenyl pentane, 4-hydroxybenzoic α-phenylbenzyl ester, phenylpropyl 4-hydroxybenzoate, phenethyl 4-hydroxybenzoate, p-chlorobenzyl 4-hydroxybenzoate, p-methoxybenzyl 4-hydroxybenzoate, 4-hydroxybenzoic benzyl ester, 4-hydroxy-2',4'-dimethyldiphenyl sulfone, β-phenethylorsellinate, cinnamyl orsellinate, orsellinic-o-chlorophenoxyethyl ester, o-ethylphenoxyethyl orsellinate, o-phenylphenoxyethyl orsellinate, 2,4-dihydroxybenzoic-β-3'-t-butyl-4'-hydroxyphenoxyethyl ester, stearyl gallate, 4-N-benzylsulfamoyl phenol, 2,4-dihydroxybenzoic-β-phenoxyethyl ester, 2,4-dihydroxy-6-methylbenzoic benzyl ester, allyl bis-4-hydroxyphenyl acetate, ditolyl thiourea, 4,4'-diacetyldiphenyl thiourea, 3-phenyl salicylic acid, 5-p-μ-methylbenzyl salicylic acid, 5-p-methoxyphenoxyethyloxy salicylic acid, 5-phenoxyethoxy salicylic acid, 5-p-benzyl-μ-methylbenzyl salicylic acid, 3-xylyl-5-(μ,μ-dimethylbenzyl)salicylic acid, 3,5-di-(α-methylbenzyl)salicylic acid, 2-hydroxy-1-μ-ethylbenzyl-3-naphthoic acid, 3,5-di-cyclopentadienyl salicylic acid, p-hydroxybenzoic-β-phenoxybutyl ester, p-hydroxybenzoic-δ-phenoxybutyl ester, 2,4,6-trihydroxybenzoic-β-p-butoxyphenoxyethyl ester, p-hydroxybenzoic-β-phenoxyethoxyethyl ester, p-hydroxybenzoic-β-p-butoxyphenoxyisopropyl ester, 2,4-dihydroxybenzoic-β-p-methoxyphenoxyethoxyethyl ester, orsellinic phenoxybutyl ether, β-resorcylic-p-methoxyphenoxyethyl ether, orsellinic-β-p-methoxyphenoxyethoxyethyl ether, orsellinic-β-o-methoxyphenoxyethyl ether, orsellinic trioxyetnyl ester, orsellinic-β-p-methoxyphenoxypropyl ester, β-resorcylic phenoxyethyl ether, β-resorcylic-δ-p-methoxyphenoxybutyl ester, phenylphenol-formaldehyde resin, and p-butylphenol-acetylene resin; polyvalent metal salts formed of these organic developers with zinc, magnesium, aluminum, and calcium; and inorganic developers such as acid clay, activated clay, attapulgite, aluminum silicate, magnesium silicate, zinc rhodanate and compolexes thereof, and zinc chloride.

Two or more of the developers enumerated above may be used in combination. Any of these developers may be used in combination with one or more members selected from the group consisting of inorganic developers such as iron stearate, cobalt naphthenate, nickel peroxide, and ammonium suflfate, aliphatic carboxylic acids such as oxalic acid, maleic acid, tartaric acid, citric acid, succinic acid, and stearic acid, and other organic acids such as benzoic acid, para-tertiary butylbenzoic acid, phthalic acid, and gallic acid. Of the electron-accepting compounds enumerated above, bisphenols, metal salts, particularly zinc salts, of salicylic acid derivatives, and zinc rhodanate complexes are particularly preferably used in the present invention.

The colorless dye polymer of the present invention is easily obtained in the form of fine particles and is capable of color formation on contact with an electron-accepting compound. It is, therefore, a high-molecular compound highly useful for heat-sensitive paper, pressure-sensitive paper, light- and pressure-sensitive paper, electorthermo-recording paper, and transfer type thermal paper, for example.

For use in the heat-sensitive paper, for instance, the colorless dye polymer in the form of fine particles produced by emulsion polymerization and an electron-accepting compound are blended in combination with a binder and the resultant mix is applied on a support to produce a recording material. The weight ratio of the colorless dye polymer to the electron-accepting compound is in the range of about 1:10 to 10:1, preferably about 1:5 to 2:3. In this case, they may be used in combination with an aromatic ether compound such as, for example, the aromatic alkyl or substituted alkyl ether compound disclosed in Japanese Patent Application (OPI) Nos. 57989/83 and 87094/83. Specific examples of the ether compound include phenoxyethyl biphenyl ether, phenethyl biphenyl, benzyloxy naphthalene, benzyl biphenyl, di-m-tolyloxy ethane, β-phenoxyethoxy anisole, 1-phenoxy-2-p-ethylphenoxy ethane, bis-β-(p-methoxyphenoxy)ethoxy methane, 1-tolyloxy-2-p-methylphenoxy ethane, 1,2-diphenoxy ethane, 1,4-diphenoxy butane, bis-β-(p-ethoxyphenoxy)ethyl ether, 1-phenoxy-2-p-chlorophenoxy ethane, 1-4'-methylphenoxy-2-4''-fluorophenoxy ethane, 1-phenoxy-2-p-methoxyphenyl thioether, 1,2-bis-p-methoxyphenyl thioethane, and 1-tolyloxy-2-p-methoxyphenyl thioethane. This ether compound is used along with the colorless dye polymer of the present invention or with the electron-accepting compound in a finely dispersed state. From the viewpoint of preventing the phenomenon of fogging, it is particularly desirable to use the ether compound in a dispersion with the colorless dye polymer. The amount of the ether compound to be used preferably does not exceed about 300% by weight, and more preferably falls in the range of about 10 to 150% by weight, based on the amount of the electron-accepting compound.

The coating liquid can also contain optional conventional additives selected to fulfil various requirements.

For example, an inorganic pigment or an oil-absorbing substance such a polyiurea filler is typically dispersed in advance in the binder for the purpose of preventing the recording head from being soiled during the course of recording. For the purpose of enhancing the release of the recording material from the recording head, a fatty acid or a metallic soap can be added to the binder in advance of the preparation of the coating liquid, and for the purpose of improving the storage stability of the colored image, hindered phenols can be added to the binder. Typically, a recording material contains such additives as a pigment, wax, antistatic agent, ultraviolet ray absorbent, defoaming agent, electroconductive agent, fluorescent dye, and surfactant, which are applied on a support in addition to the colorless dye and the electron-accepting compound which directly contribute to color formation.

Specific examples of useful pigments include kaolin, calcined kaolin, talc, zinc oxide, amorphous silica, calcium carbonate, aluminum hydroxide, magnesium hydroxide, calcined plaster, silica, magnesium carbonate, titanium dioxide, alumina, barium carbonate, barium sulfate, mica, microballoons, urea-formalin filler, polyethylene particles, and cellulose filler. One or more of these pigments can be used in the form of particles measuring about 0.1 to 15 μm in diameter.

Examples of suitable waxes include paraffin wax, carboxy-modified paraffin wax, carnauba wax, microcrystalline wax, polyethylene wax, and higher fatty acid esters.

Examples of the metallic soap include ppolyvalent metal salts of higher fatty acids including zinc stearate, aluminum stearate, calcium stearate, and zinc oleate.

Hindered phenols are compounds containing at least one bulky group in a position adjacent to a phenolic hydroxyl group, such as polybutylated bisphenol A and 1,1,3-tris-3-t-butyl-4-hydroxy-6-methylphenyl butane.

Such additives are dispersed in a binder, and the binder generally is soluble in water. Examples of the binder include polyvinyl alcohol, hydroxyethyl cellulose, hydroxypropyl cellulose, epichlorohydrin-modified polyamide, ethylene-maleic anhydride copolymer, styrene-maleic anhydride copolymer, isobutylene-maleic anhydride copolymer, polyacrylic acid, polyacrylic acid amide, methylol-modified polyacrylamide, starch derivatives, casein, and gelatin. The binder, for the purpose of reducing water solubility may incorporate therein a waterproofing agent (gelling agent or cross-linking agent) or the emulsion of a hydrophobic polymer, specifically a styrene-butadiene rubber latex or acylic resin emulsion.

Further, for the purpose of imparting chemical resistance to the surface of the coated layer, a layer formed of a water-soluble high-molecular compound such as, for example, polyvinyl alcohol, hydroxyethyl starch, or epoxy-modiified polyacrylamide and a gelling agent (hardening agent) in a thickness in the range of about 0.2 to 2 μm may be superposed on the recording layer.

The coating liquid, generally, is coated on base paper, high-grade paper, or synthetic paper, each preferably of neutral quality.

Generally, the amount of the coating liquid coated to form a recording layer falls approximately in the range of 2 to 10 g/m² as solids.

For use in the heat-sensitive paper, the coating liquid may be in any of the various forms as disclosed in West German Patent Application (OLS) Nos. 2,228,581, and 2,110,854, and Japanese Patent Publication No. 20142/77. This heat sensitive paper may be preheated, wetted to a prescribed level, or stretched in advance of use in recording.

For use in a pressure-sensitive paper, the coating liquid may be in any of the various forms disclosed in U.S. Pat. Nos. 2,505,470, 2,505,471, 2,505,489, 2,548,366, 2,712,507, 2,730,456, 2,730,457, 3,103,404, 3,418,250, and 4,010,038. Generally, this pressure-sensitive paper consists of a pair of sheets, one containing the colorless dye and the other containing electron-accepting compound.

For the manufacture of microcapsules to be used in the pressure-sensitive paper, a method employing coacervation of a hydrophilic colloid sol disclosed in U.S. Pat. Nos. 2,800,457 and 2,800,458; a method of interfacial polymerization disclosed in British Pat. Nos. 867,797, 950,443, 989,264, and 1,091,076; or a method disclosed in U.S. Pat. No. 3,103,404 may be used.

A color forming sheet, generally, is obtained by dissolving one colorless dye or two or more colorless dyes in a mixed state in a solvent (a synthetic oil such as an alkylated naphthalene, alkylated diphenyl, alkylated diphenyl methane, alkylated terphenyl, or chlorinated paraffin; a vegetable oil such as cotton seed oil or castor oil; an animal oil; a mineral oil; or a mixture thereof), filling microcapsules with the resultant solution, and coating the filled microcapsules on a transparent or opaque smooth support such as paper, high-grade paper, plastic sheet, or resin-coated paper.

A developing sheet is obtained by dispersing one electron-accepting compound or two or more such compounds in a mixed state, optionally in combination with other electron-accepting compounds, in a binder such as, for example, a styrene-butadiene latex or polyvinyl alcohol and coating the resultant dispersion in combination with a pigment described above on a support such as paper, a plastic sheet, or resin-coated paper.

The amounts of the colorless dye and the electron-accepting compound used depend on the thickness of the coated layer, the form of the pressure-sensitive copying paper, the method for manufacture of microcapsules, and other conditions and, is easily determined and selected in accordance with such conditions. For persons skilled in the art, it is easy to determine these amounts.

An electrothermo-recording paper is produced by the method disclosed in Japanese Patent Application (OPI) Nos. 11344/74 and 48930/75, for example. The electro-thermo-recording paper is generally produced by preparing a coating liquid having an elecrroconductive substance, the colorless dye polymer of the present invention and the electron-accepting compound dispersed in combination with a binder and applying this coating liquid on a support such as paper, or by applying the electroconductive substance on the support thereby forming an electroconductive layer and then applying thereon a coating liquid containing the colorless dye polymer of the present invention, the electron-accepting compound, and the binder. Optionally, the heat-fusible substance as described in U.S. patent application Ser. No. 06/872,785 may be additionally used for the purpose of enhancing the sensitivity of the electro-thermo-recording paper.

A light- and pressure-sensitive paper is produced, for example, by the method disclosed in Japanese Patent Application (OPI) No. 179836/82. Generally, the colorless dye and optionally a solvent are sealed in microcapsules of a wall of synthetic resin such as polyether urethane or polyurea in combination with a photopolymerization initiator such as silver iodobromide, silver bromide, silver behenate, Michler's ketone, benzoin derivative, or benzophenone derivative and a cross-linking agent of a polyfunctional monomer such as a polyallyl compound, poly(meth)acrylate, or poly(meth)acrylamide. After imagewise exposure, the colorless dyes present in unexposed areas, when brought into contact with a color developer (electron-accepting compound), result in coloration.

The polymerizable colorless dye monomer according to the present invention can be synthesized by various methods. It is obtained, for example, by reacting a corresponding benzoylbenzoic acid or benzoylpyridinecarboxylic acid with indole or by reacting a corresponding carboxybenzoyl indole or carboxypyridinecarbonyl indole with an aniline derivative in the presence of a condensing agent such as acetic anhydride or phosphorus oxychloride, when necessary, in a volatile organic inert solvent such as chloroform, benzene, or chlorobenzene at a reaction temperature in the range of 50° C. to 140° C. for a period of 10 to 120 minutes. Then the reaction product is placed in ice water thereby effecting hydrolysis of the condensing agent. A volatile organic inert solvent added to the reaction system; the resultant solution is rendered alkaline with an aqueous solution of sodium hydroxide; the solvent layer is separated; and the separated solvent layer is distilled under a vacuum to remove the solvent. Preferably production is conducted by a method using an m-substituted aminophenol or m-substituted aminophenoxy ethanol as a starting material, thereby preparing an aminophenol derivative having an addition polymerizable group, and then reacting carboxybenzoyl indole or carboxy-pyridinecarbonyl indole with the aminophenol derivatie.

For this reaction, any conventional method can be adopted. For example, the reaction conditions are disclosed in Japanese Patent Application (OPI) No. 168664/86.

SYNTHESIS EXAMPLE 1

Synthesis of
3-(4-diethylamino-2-β-methacryloyloxy-ethoxy-phenyl)-3-(1-ethyl-2-methylindol-3-yl)phthalide In a flask, 0.05 mol of m-diethylaminophenoxyethyl methacrylate and 0.05 mol of 3-o-carboxybenzoyl-1-ethyl-2-methylindole obtained by the reaction of 1-ethyl-2-methyl indole with phthalic anhydride were combined and the resultant mixture and 20 ml of acetic anhydride added thereto were heated to 85° C. The reaction immediately began to proceed and the reaction system assumed a bluish purple color. The reaction product was poured in water and separated by column chromatography using a chloroformethyl acetate mixture. The desired product was obtained in the form of white crystals having a melting point of 173° C. to 174° C.

SYNTHESIS EXAMPLE 2

Synthesis of
3-(4-diethylamino-2-β-methacryloyloxy-ethoxy-phenyl)-3-(1-octyl-2-methylindol-3-yl)phthalide The desired product was obtained by repeating the procedure of Synthesis example 1, excepting for using 1-octyl-2-methyl indole instead of 1-ethyl-2-methyl indole. The melting point of this product was 89° C. to 91° C.

SYNTHESIS EXAMPLE 3

Synthesis of
3-[4-diethylamino-2-vinylbenzyloxyphenyl]-3-(1-ethyl-2-methylindol-3-yl)phthalide A reaction was carried out following the procedure of Synthesis example 1, except for using m-diethylaminophenoxymethyl styrene instead of m-diethylaminophenoxyethyl methacrylate.

The coarse product was in an oily state and assumed a bright bluish purple color on silica gel.

The m-diethylaminophenoxymethyl styrene was obtained by reacting m-diethylaminophenol with chloromethyl styrene (as a mixture) in the presence of potassium carbonate.

The present invention will be described more specifically below with reference to working examples. However, this invention is not to be construed as being limited to the examples. Unless otherwise indicated, all parts, percents and ratios are by weight.

EXAMPLE 1

In a flask equiped with a nitrogen gas inlet tube, 0.5 g of 3-(4-diethylamino-2-β-methacryloyloxyethoxyphenyl)-3 -(1-ethyl-2-methylindol-3-yl)phthalide, 0.1 g of divinyl benzene, and 0.1 g of 2-ethylhexyl methacrylate were placed, 20 ml of tetrahydrofuran and 5 ml of methylethyl ketone were introduced therein, and nitrogen gas was introduced to agitate the contents of the flask for 25 minutes. Then, the contents, with 15 mg of azo-bis-dimethyl isovaleronitrile added thereto, were left standing at 60° C. to 65° C. for six hours while nitrogen gas was gently bubbled therethrough. At the end of this reaction, the contents of the flask were poured into 400 ml of methanol. Consequently, a high-molecular compound was precipitated.

In a sand mill, the precipitate and 25 g of an aqueous 3.5% polyvinyl alcohol (saponification degree 99% and polymerization degree 1,000) solution were dispersed into particles having an average particle diameter of 2 μm.

Separately, 10 g of β-phenoxyethyl orsellinate, and 8 g of β-naphtholbenzyl ether were dispersed in combination with 50 g of an aqueous 3% polyvinyl alcohol solution in a ball mill overnight. Further, 8 g of β-p-methoxyphenoxyethyloxy salicylic acid, 10 g of zinc oxide, and 13 g of 1-phenoxy-2-p-ethylphenoxy ethane were dispersed overnight in combination with 50 g of an aqueous 3% polyvinyl alcohol solution in a ball mill. Then, 0.1 g of 1,1,3-tris-2'-methyl-4'-hydroxy-5'-t-butylphenyl butane and 20 g of an aqueous 5% polyvinyl alcohol solution were dispersed overnight.

The dispersions obtained as described above were mixed thoroughly. Then, the resultant mixture and 15 g of Georgia kaolin and 6 g of finely divided amorphous silica added thereto were thoroughly dispersed. The dispersion consequently obtained was mixed with 4 g of a dispersant (produced by Chukyo Oils and Fats Co. and marketed under trademark designation of "Cellosol #428"), to produce a coating liquid.

This coating liquid was applied in a ratio of 5.5 g/m$^2$ as solids on a neutral paper having a basis weight of 45 g/m$^2$, dried at 60° C. for one minute, and then subjected to super-calendering at a linear pressure of 60 kgW/cm, to produce a coated paper.

The coated paper was treated in a facsimile unit at a heating energy of 35 mJ/mm$^2$ for color formation and then tested for color density with a Macbeth reflection densitometer. The density was found to be 1.0.

The recording material thus obtained was not fogged during storage and exhibited highly satisfactory stability to withstand aging. The image obtained on the recording material was a bright black color and showed satisfactory resistance to chemicals, water, and sunlight.

EXAMPLE 2

A coating liquid was obtained by following the procedure of Example 1, except for using hexyl acrylate instead of 2-ethylhexyl methacrylate, and benzyl p-hydroxybenzoate instead of β-phenoxyethyl orsellinate. On a pigment-containing paper obtained by superposing calcium carbonate on a neutral paper, the coating liquid was coated in a ratio of 6 g/m$^2$ and dried in the same manner as in Example 1.

When the recording material consequently obtained was tested following the procedure of Example 1, there was produced a bright black image. The reflection density was at least 0.95.

This black image was clear and showed outstanding resistance to discoloration due to exposure to fats and oils and sunlight.

EXAMPLE 3

As monomers, 0.5 g of 3-(4-diethylamino-2-β-methacryloyloxyethoxyphenyl)-3-(1-ethyl-2-methylindol-3-yl)phthalide, 0.2 g of 2-acrylamino-6-diethylaminofluoran, and 0.5 g of butyl methacrylate were placed in a flask containing 20 ml of tetrahydrofuran and 5 ml of methylethyl ketone and equiped with a nitrogen gas inlet tube, and the mixture was agitated with nitrogen gas for 25 minutes. Then, the contents of the flask, with 15 mg of azo-bis-dimethylisovaleronitrile added thereto, were left standing at 60° to 65° C. for six hours with gentle bubbling therethrough of nitrogen gas. When the contents of the flask were poured into 400 ml of methanol, there was precipitated a high-molecular compound. The amount of the produced compound was 1 g.

EXAMPLE 4

A coating liquid was obtained by following the procedure of Example 3, except for using 0.3 g of butyl methacrylate, 0.1 g of styrene, 0.3 g of 2-p-vinylbenzoylamio-3-methyl-6-diethylaminofluoran, and 0.3 g of 3-(4-diethylamino-2-β-methacryloyloxyethoxyphenyl)-3-(1-octyl-2-methylindol-3-yl)phthalide as starting monomers. The reaction time was changed to eight hours and the post-treatment was carried out in the same manner as in Example 1. When the contents of the flask after the reaction were poured into 400 ml of methanol, a high-molecular compound was obtained as a precipitate. The amount of the produced compound was 0.8 g.

The copolymer consequently obtained assumed a bright color on contact with zinc 3,5-α-methylbenzyl salicylate or Silton clay. The colored image showed highly satisfactory preservability.

EXAMPLE 5

In a three-neck flask equiped with a stirrer and a thermometer and containing 250 ml of water, a solution of 5 g of butyl acrylate and 5 g of 3-(4-diethylamino-2-β-methacryloyloxyethoxyphenyl)-3-(1-octyl-2-methylindol-3-yl)phthalide in 45 ml of ethanol was emulsified and dispersed. As an emulsifier, 1 g of methyloleyl taurate was used. The dispersion was agitated with nitrogen gas and, under vigorous stirring, was mixed with 1 wt % of a radical polymerization initiator, $K_2S_2O_8$, and then left standing a 70° C. for four hours. During the course of the polymerization reaction, ethanol was expelled from the system.

Thus, there was obtained a dispersion of an emulsion copolymer of the polymerizable colorless dye and the monomers. The average particle diameter was 81 Å.

This dispersion was labeled as Emulsified Liquid (A).

Separately, a dispersion of an electron-accepting compound having a particle diameter of 2 μm was obtained by dispersing 1.0 part by weight of 5-β-p-methoxyphenoxyethoxy salicylic acid and 1.1 parts by weight of zinc oxide in 0.02 part of PVA-105 (produced by Kuraray Co., Ltd.) and 10 parts of water with a horizontal sand mill.

The aforementioned emulsified liquid (A) and the electron-accepting compound were mixed in respective amounts such that the emulsified liquid had a relative weight of 0.5 part as solids and the calcium carbonate and the zinc stearate had relative weights of 1.5 parts and 0.25 part, respectively, as solids, and stirred thoroughly, with 0.3 part of PVA-105 (produced by Kuraray Co., Ltd.) added thereto.

On a smooth support having finely divided calcium carbonate and stearic acid amide (weight ratio 5:1) applied in a basis weight of 5 g/m$^2$ on a neutral paper, the liquid resulting from the stirring was applied in a ratio of 5 g/m$^2$.

When the recording material consequently obtained was treated in a facsimile unit for color formation by following the procedure of Example 1, the image had a density of 1.2. The temperature at which color formation began was 103° C. The fog was not more than 0.1. When the dispersion of the emulsion copolymer was used, the produced recording material exhibited highly satisfactory properties.

EXAMPLE 6

A recording material was obtained by following the procedure of Example 5, except that bisphenol A and β-benzyloxy naphthalene were used in the place of 5-β-p-methoxyphenoxyethoxy salicylic acid and zinc oxide, respectively.

The recording material consequently obtained produced a bright colored image.

While the invention has been described in detail and with reference to specific embodiments thereof, it will be apparent to one skilled in the art that various changes and modifications can be made therein without departing from the spirit and scope thereof.

What is claimed is:

1. A recording material comprising a support having thereon a recording layer comprising an at least one electron-donating colorless dye and at least one electron-accepting compound, wherein said electron-donating colorless dye is a copolymer of at least one polymerizable colorless dye monomer and at least one comonomer, wherein said polymerizable colorless dye monomer contains at least one addition polymerizable group, and wherein said addition polymerizable group is selected from an acrylic ester group, a methacrylic ester group, an allyl group, or a vinyl group.

2. The recording material as claimed in claim 1, wherein said addition polymerizable group is an acrylic ester group or a methacrylic ester group.

3. The recording material as claimed in claim 2, wherein said acrylic ester group is an acryloyloxyalkyl group or an acryloyloxyaryl group.

4. The recording material as claimed in claim 2, wherein said methacrylic ester group is a methacryloyloxyalkyl group or a methacryloyloxyaryl group.

5. The recording material as claimed in claim 1, wherein said polymerizable colorless dye monomer is represented by formula (I):

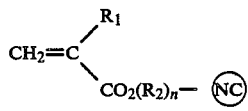

(I)

wherein $R_1$ represents a hydrogen atom, a methyl group or an ethyl group, $R_2$ represents an alkylene group which may include at least one oxygen or sulfur atom, an alkenylene group, or an arylene group, each having 2 to 10 carbon atoms, n is 0 or 1, and ⓃⒸ represents a basic dye moiety of a non-polymeric colorless dye selected from triphenyl methane phthalide type compounds, fluoran type compounds, phenothiazine type compounds, indolyl phthalide type compounds, leucoauramine type compounds, rhodamine lactam type compounds, triphenyl methane type compounds, and triazene type compounds.

6. The recording material as claimed in claim 1, wherein said polymerizable colorless dye monomer is present in said copolymer in an amount of 10 to 80 mol %.

7. The recording material as claimed in claim 1, wherein said comonomer is present in said copolymer in an amount of 80 mol % or less.

8. The recording material as claimed in claim 7, wherein said comonomer is present in said copolymer in an amount of 50 mol % or less.

9. The recording material as claimed in claim 1, wherein said copolymer is a latex containing particles having an average diameter of not more than about 1 μm.

10. A recording material as in claim 1, wherein said copolymer is a monomer copolymerizable with the polymerizable colorless dye and contains at least one addition copolymerizable group selected from the group consisting of a vinyl group, an acrylic group, a methacrylic group, an allyl group, and a vinylidene group.

* * * * *